United States Patent [19]

Busch et al.

[11] Patent Number: 5,612,218

[45] Date of Patent: Mar. 18, 1997

[54] METHOD OF HANDLING BIOLOGIC MATTER AND MEANS FOR CARRYING OUT THE METHOD

[76] Inventors: Christer Busch, Nya Valsatravagen 17, S-756 46 Uppsala; Ingrid Backlund, Norrtaljegatan 9B, 8-753 27 Uppsala, both of Sweden

[21] Appl. No.: 229,719

[22] Filed: Apr. 19, 1994

Related U.S. Application Data

[63] Continuation-in-part of Ser. No. 801,880, Dec. 3, 1991, abandoned.

[51] Int. Cl.⁶ .............................. C12M 1/24; C12N 5/06; C12Q 1/24
[52] U.S. Cl. .................... 435/288.1; 435/40.52; 435/307.1
[58] Field of Search .................... 435/286, 296, 435/1, 3, 288.1, 304.1, 307.1, 40.52; 427/4; 425/117

[56] References Cited

U.S. PATENT DOCUMENTS

| | | | |
|---|---|---|---|
| 3,371,012 | 2/1968 | Furuhashi | 435/1 |
| 3,674,396 | 7/1972 | McCormick | 425/117 |
| 4,061,537 | 12/1977 | Seiler et al. | 435/1 |
| 4,569,647 | 2/1986 | McCormick | 435/284 |
| 4,572,899 | 2/1986 | Walker et al. | 435/240.3 |
| 4,588,579 | 5/1986 | Bachhuber et al. | 435/1 |
| 4,695,536 | 4/1987 | Lindstrom et al. | 435/1 |
| 4,713,375 | 12/1987 | Lindstrom et al. | 514/57 |
| 4,786,601 | 11/1988 | Rothenberg | 435/284 |
| 4,857,300 | 8/1989 | Maksem | 435/1 |
| 5,104,787 | 4/1992 | Lindstrom et al. | 435/1 |
| 5,272,136 | 12/1993 | Takruri | 514/21 |

FOREIGN PATENT DOCUMENTS

| | | | |
|---|---|---|---|
| 8903051 | 3/1991 | Sweden . | |
| 1012856 | 4/1983 | U.S.S.R. | 435/1 |
| 1416733 | 12/1975 | United Kingdom . | |

OTHER PUBLICATIONS

Abstract of Swedish Patent 8903051 (Mar. 16, 1991).
Hayat, ed., Principles and Techniques of Scanning Electron Microscopy, published by Van Nostrand (NY), vol. 4, pp. 8–13.
Lennette et al, eds., Manual of Clinical Microbiology, 2nd ed., published 1974 by American Society For Microbiology (Washington, D. C.), pp. 940–941.

Primary Examiner—Jeffrey E. Russel
Attorney, Agent, or Firm—Ostrolenk, Faber, Gerb & Soffen, LLP

[57] ABSTRACT

The present invention relates to a standardized method of handling tissue samples taken with the aid of a sampling instrument and also to other biologic matter, such as, for example, intact portions of a living organism such as a heart, finger and the like. The invention is characterized in that the tissue sample or other biologic matter is transferred to an isosmotic, atoxic, pyrogen-free, semi-viscous, sterile, freezable liquid whose density corresponds approximately to the density of the sample or other biologic matter. The means for carrying out the method is characterized by a plastic tube filled with the aforesaid liquid.

9 Claims, 3 Drawing Sheets

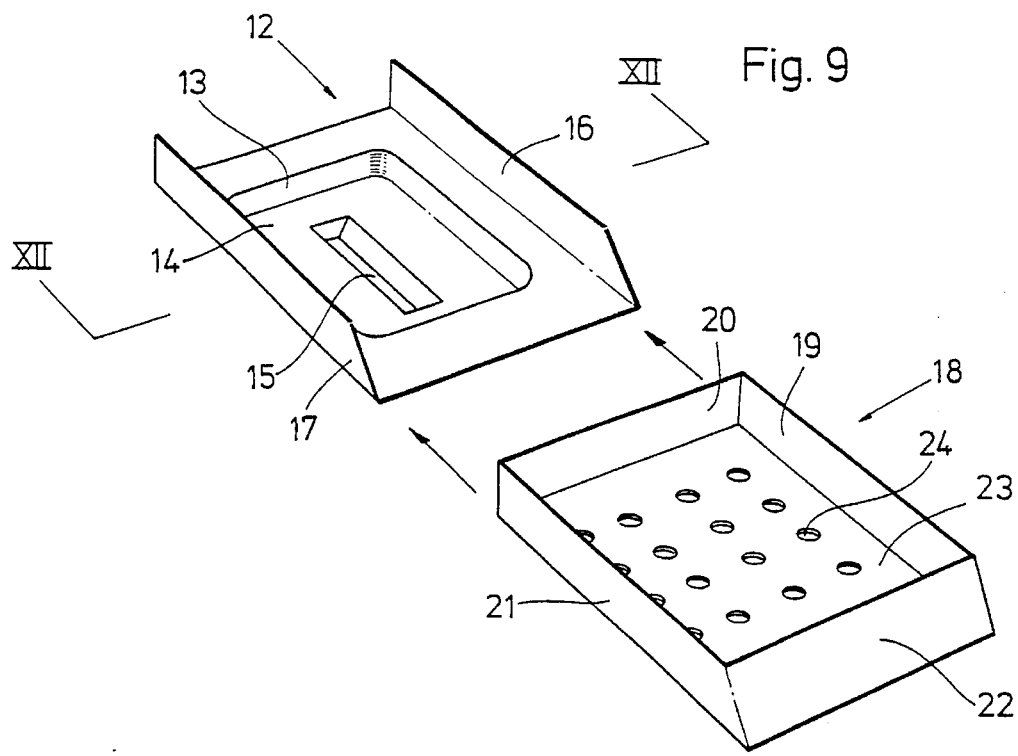
Fig. 9
Fig. 10
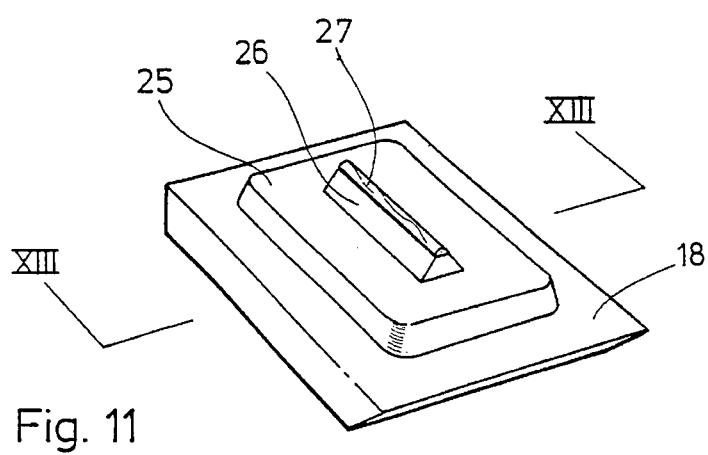
Fig. 11
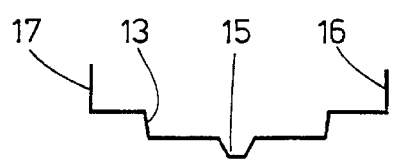
Fig. 12
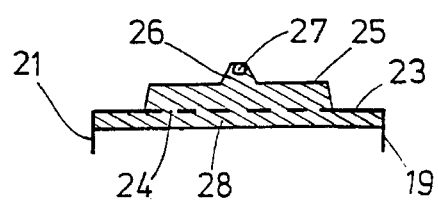
Fig. 13

METHOD OF HANDLING BIOLOGIC MATTER AND MEANS FOR CARRYING OUT THE METHOD

This application is a continuation-in-part of application Ser. No. 07/801,880 filed Dec. 3, 1991, now abandoned.

There is at present no standardized procedure for handling tissue samples that have been taken with the aid of sampling instruments, such as biopsy needles, pincettes, etc. The sample is normally placed in a vessel that contains a so-called physiological salt solution and remains in the solution. Alternatively, the sample is placed in a fixative fluid. The thus preserved tissue sample is then sent to a pathological laboratory, where it is analyzed in accordance with known methods. Such handling of tissue samples is unsatisfactory, since the samples may be subjected to contamination and mechanical influences in conjunction with the deposition and/or transportation of the samples.

The tissue sample is prepared for analysis in the laboratory according to one of two different methods. If the sample is fixed, it is subjected to a leaching process and then embedded in a paraffin block, subsequent to having been positioned on a flat-bottom mould, this positioning or orientating of the sample often being imperfect. The tissue sample is then cut into thin sections with the aid of a microtome and placed on a slide. If the sample has not been fixed prior to arriving at the laboratory, it is transferred to a so-called freeze table on which the sample is frozen solid in a gel composed for this purpose. The tissue sample is then cut by means of a microtome into a number of so-called frozen sections and the sections are placed on a slide.

When the tissue sample is taken with the aid of a biopsy needle, the sample will have the form of a cylinder with a diameter of 0.9–1.2 mm and a length of up to about 25 mm. It is necessary to release the sample from the needle in a sterile and non-toxic environment, normally in a physiological, sterile salt solution whose density is close to the density of water. This separation of the sample from the needle into the physiological liquid, or in the worst of cases to a dry air environment, involves the risk of the sample being subjected to mechanical influences and also to the risk of the sample drying out. Such a tissue sample lacks dimensional stability and cannot therefore be placed manually on the freeze table or in the flat bottom paraffin mould in a straight, horizontal position without difficulty, and the sample is therefore liable to be destroyed mechanically. If an attempt is made to lift the sample with the aid of pincettes and the sample then straightened out to a horizontal position on the freeze table or in the flat bottom paraffin mould, there is a risk that the sample will rupture. Rather than risk rupturing of the sample, the sample is left lying on the freeze table in a position which is not fully horizontal when freezing the sample or when the sample is cast in paraffin. FIG. 7 illustrates an example of a tissue sample which is not positioned horizontally. Subsequent to being frozen or cast in paraffin, the sample has the appearance shown in FIG. 7, and a slice cut along the broken line will result in a number of sample fragments. It is desirable, however, to obtain a single elongated and continuous section of tissue sample.

The object of the present invention is to avoid the drawbacks associated with the known technique and relates to a method of handling tissue samples in a standardized fashion. When taking a tissue sample, the sample shall be transferred to a vessel or container in which the sample is protected microbiologically, chemically and mechanically. To this end, the container is filled with a semi-viscous liquid, the properties of which are defined in the following claims. The composition of the liquid is such as to ensure that the tissue sample will constantly be surrounded by a protective film or a protective liquid volume. In the majority of cases, the sample will be held suspended in the liquid, a gyro-like effect which contributes to the protection afforded the sample. The container will preferably have the shape of a test tube and can be sealed with the aid of a cap or stopper. The sample floats freely in the semi-viscous liquid and the container can thus be transported from the place where the sample was taken to the pathological laboratory and subjected to normal knocks and blows during transportation without the sample degenerating as a result of these knocks and blows on the container, within reasonable limits. If the transportation of distance is long in both time and space, the sample may be fixed in the container, prior to being sent to the laboratory. A fixed sample can be readily distinguished from a non-fixed sample upon its arrival at the laboratory and during subsequent handling of the sample therein.

The object of the present invention is also to provide a means for handling other types of biologic matter in a manner which not only protects the biologic matter from shocks and mechanical trauma during, for example, transport procedures, but also maintains the morphologic characteristics of the biologic matter. This is particularly important, for example, in handling intact portions of a living organism such as a heart, finger and the like. To this end, the present invention relates to handling biologic matter such as cells, embryos, oocytes, bacterial samples, viral samples, serum, organ samples and the like. In particular, in addition to being of interest regarding the handling of a tissue sample which has been taken with the aid of a sampling instrument such as a biopsy needle and the like, the present invention is directed to any application which relates to the handling of biologic matter where the preservation of morphologic characteristics is required. The term "handling" is meant to include retrieving, transporting, preserving, cultivating, storing and/or processing of biologic matter such as tissue samples, cells, embryos, oocytes, bacterial samples, vital samples, serum, biopsy samples, organ samples and the like.

The object of the present invention is also to provide a liquid with respect to which the osmotic and colloid osmotic activity of the solution does not interfere and impair the results of subsequent pathological examination of the tissue sample. In addition, the freezing behavior must be satisfactory when the tissue sample is frozen in the usual manner, and the solution should be compatible with use of fixation chemicals such as formalin, paraformaldehyde, glutaraldehyde and other fixation agents or components in the fixation solution. It is also desirable that the liquid exhibit a good compatibility in the event that a minute amount be introduced into the body in those instances when the biopsy needle is repeatedly used for sampling another biopsy.

The present invention also relates to means which will enable a tissue sample to be oriented in a plane-parallel position, hereinafter referred to as sample levelling, on a freeze table or when cast in a paraffin mould, and then firmly mounted on the holder of the cryostat or the microtome. The sample can then be cut without suffering tissue losses as a result of oblique or crooked positioning of the frozen sample, thereby enabling a number of frozen sections, all continuous, to be taken ("planed") from one and the same sample.

A sample arriving at the laboratory may also be frozen for storage in a sample bank. The invention prevents dehydration of the sample and contamination of the surroundings by the actual sample itself.

When samples are taken with the aid of biopsy needle, one and the same needle assembly can be used to take several tissue samples one after the other.

The aforesaid objects are achieved by means of the present invention described herein.

The invention will now be described in more detail with reference to a number of exemplifying embodiments thereof and also with reference to the accompanying drawings, in which FIG. 1 is a perspective view of a container filled with liquid in accordance with the invention;

FIG. 9 illustrates a different type of shell mould used to embed the tissue sample in paraffin;

FIG. 10 illustrates in perspective a carrier element used together with the mould shown in FIG. 9;

FIG. 11 is a perspective view of an assembly having a paraffin-embedded sample on the carrier element;

FIG. 12 is a cross-sectional view of the mould shown in FIG. 9, taken on the line XII—XII; and FIG. 13 is a cross-sectional view of the assembly shown in FIG. 11, taken on the line XIII—XIII.

Figure 1:
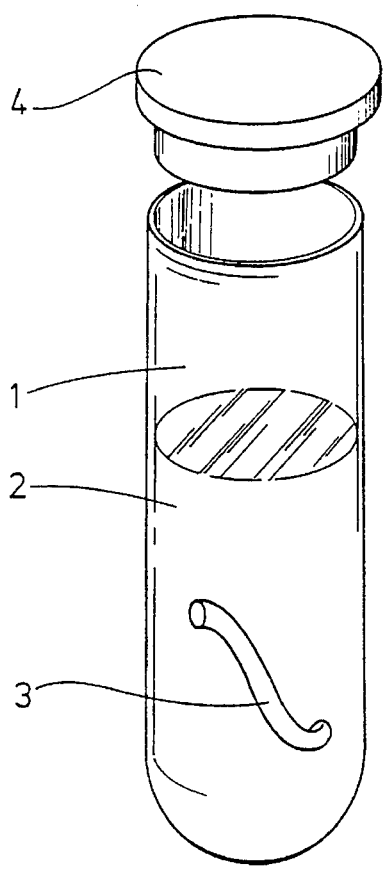

Shown in FIG. 1 is a test tube container 1 which is filled with liquid 2 in which a specimen 3 such as a tissue sample is freely suspended. The container 1 can be closed by means of a cap or stopper 4.

The container 1 is produced from thin-gauge, non-toxic and pyrogen-free plastic which can withstand conventional sterilization processes, high temperatures (boiling) and very low temperatures, e.g. freezing down to cryogenic temperatures, without cracking.

The liquid must be incapable of damaging the sample and shall generally be tissue compatible. The liquid is also isosmotic with the tissue, i.e. about 300 mosm/l, atoxic, pyrogen free, semi-viscous, sterile, freezable, transparent, and have a density which corresponds approximately to the density of the tissue sample. The liquid has a pH-value which corresponds to the pH of the tissue, i.e. about 7.4, and is mixable with water and/or alcohol-based solvents. The liquid can also be frozen without crystals forming. The isosmotic property of the liquid means that water will neither leave nor be delivered to the tissue sample when the sample is stored in the liquid. The atoxic property of the liquid means that the tissue sample will not be contaminated chemically when stored in liquid. The sterile property means that the sampling instrument can be immersed in the liquid immediately after taking a sample, whereafter the sample is released into the liquid in a manner described in more detail below, and is thereafter removed from the liquid so that a further tissue sample can be taken with the same sampling instrument without needing to sterilize the instrument. The recited density together with the semiviscous property of the liquid means that a tissue sample deposited in the liquid will be freely suspended therein, without fastening to the wall of the sample container should the container be twisted and turned with the stopper 4 fitted into the tube. The sample 3 is constantly in suspension in the liquid 2. The viscous property of the liquid means that the liquid will dampen impact forces, thereby protecting the sample from impermissibly large shear forces or fracture forces which may result in mechanical rupture of the sample. The fact that the liquid will not form crystals when freezing, means that the tissue will not be damaged by the freezing process and that the frozen sections will have smooth and even surfaces which can be readily dyed and subsequently studied under a microscope. The liquid will also preferably be mixable with water and/or alcohol-based solvents.

The above mentioned properties of the liquid also contribute towards enabling the sample to be removed from the biopsy needle or biopsy pincettes in a careful and nontraumatic fashion.

The sterility, non-toxicity and tissue-compatibility of the liquid enables samples to be taken repeatedly with one and the same biopsy needle.

Without intending to be bound by a theory of operation, it is believed that the protection against shocks and mechanical trauma provided by the liquid or gel of the present invention is the result of the viscoelastic properties of the gel; that is, the viscous and elastic properties of the gel. For example, rapid movement of a tissue sample such as a biopsy suspended or embedded in the gel are damped by the action of the elasticity of the surrounding gel solution. The viscous property of the gel is important when the fragile biopsy sample is introduced into the gel by, for example, a biopsy needle; that is, low frequencies. On the other hand, the elastic property provides structural stabilization to the delicate biopsy sample under rapid movements; that is, at high frequencies. In other words, the liquid or gel protects the tissue both by its elastic and its viscous properties.

Viscoelastic properties (rheology properties) are best expressed and controlled by measuring essentially three different parameters, namely phase angle, storage modulus and loss modulus, which can be measured by a rheometer. At low frequencies (low movement, i.e. under gentle manipultions and mild transportation) the viscous behavior ( loss modulus ) is the dominant parameter. In the transport procedures and other rapid movements the biopsy sample may be exposed to a more rough treatment. In these treatments the elastic property ( storage modulus ) is important and protects the sample from damage. One way to construct such a viscoelastic solution is to make an aqueous solution of very large molecules (polymers) or particles (dispersions).

Examples of monomers for making homo-polymers and co-polymers for the gel of the present invention include acrylamide, substituted acrylamides, acrylic acid, esterified acrylic and methacrylic acid such as hydroxyethyl methacrylate hydroxyethoxyethyl methacrylate, methoxyethyl methacrylate, methoxyethoxyethyl methacrylate. Other examples of polymers are vinyl polymers e.g. poly (vinyl pyrrolidine), poly(vinyl alcohol), poly(vinyl ethers) , poly(vinyl acetate) and various co-polymers. Also polysaccharide based derivatives might be useful, e.g. cellulose ethers and esters (methyl-,ethyl, propyl, ethoxylated, carboxylated) such as hydroxy propyl methyl cellulose (HPMC), carboxy methyl cellulose (CMC), ethyl hydroxy ethyl cellulose (EHEC), hydroxy ethyl starch (HES), xanthan, agarose, carrageenan, etc.

In the preferred embodiment, the liquid of the present invention is a gel in the form of a viscoelastic solution which comprises water soluble high molecular weight polymers. Such gel comprises hydroxypropylmethyl cellulose ("HPMC" herein) in an aqueous phosphate buffered solution. In the preferred embodiment, a particularly satisfactory gel formula includes 1.8% ±5% HPMC and 98.2% phosphate buffered solution of distilled water buffered with $KH_2PO_4$ (Merck Pro Analysis) 0.654 gram/liter, KCl (Merck Extra Pine) 0.654 gram/liter and NaCl 9.00 grams/liter, with pH adjusted to 7.4 ±0.4. The gel's viscosity is affected by the concentration of the HPMC. An undesirable increase in the viscosity of the gel will increase the colloid osmotic pressure which will effect a thermodynamic driving force which will pump out water from the biologic matter into the surrounding liquid. This will tend to undesirably dry out the biologic matter. Similary, an undesirable decrease in the viscosity of the gel will decrease the colloid osmotic pressure which will tend to undesirably infuse the biologic matter with water. By controlling the concentration of the HPMC, the viscosity of the gel may be controlled as desired. In particular, an increase in concentration of HPMC will increase the viscosity of the gel and a decrease in the concentration of the HPMC will decrease the viscosity of the gel. A preferred HPMC is sold by Dow Medical under the name, Metocel E4M Premium Grade. Heretofore, Metocel E4M Premium Grade was used in eye surgery and in connection with other ocular eye products.

In one embodiment of the method of the present invention, the tissue sample is transferred from the sample instrument to the liquid. This can be done, for example, by inserting the instrument together with the sample into the liquid. The sampling instrument is then withdrawn from the liquid, leaving the sample suspended freely therein. When the sampling instrument is a needle biopsy instrument of the type sold under the trademark TRU-CUT, the needle assembly is detached from the instrument and the outer needle then retracted so as to expose the recessed part of the inner needle in which the sample lies. When the sample has been released, the needle assembly is submerged in the liquid and the biopsy needle moved laterally, the sample therewith being released from the needle and remaining in the liquid when the needle is withdrawn therefrom. The semi-viscous state of the liquid enables the sample to be loosened from the needle by moving the needle gentle sideways, with the minimum risk of mechanical damage to the sample. A lowly viscous liquid would not offer sufficient resistance to this sideways movement of the needle to minimize the mechanical damaging effect on the sample.

One or the other of the following two procedures can now be followed, depending on the distance in time and space between the place where the tissue sample was taken and the pathological laboratory in which the tissue is to be analyzed.

Figure 2:
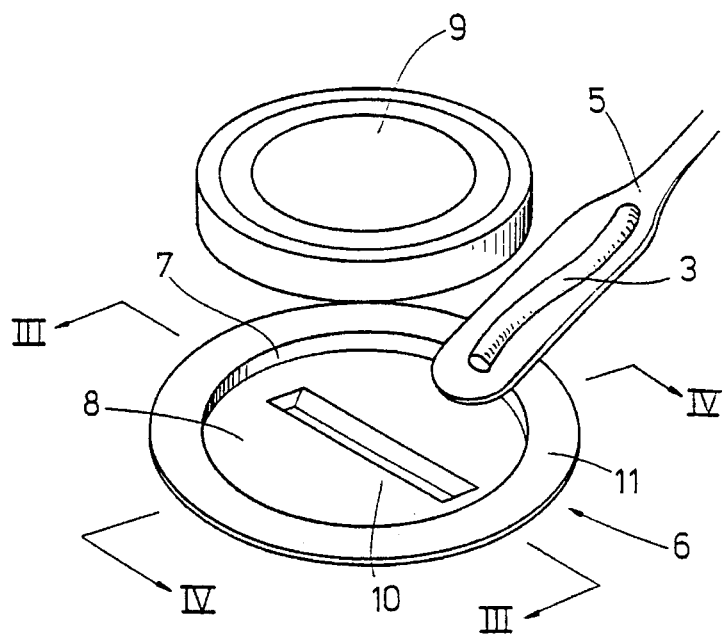
FIG. 2 illustrates in perspective a shell-mould according to the invention, in which the tissue sample is placed prior to being frozen on the freeze table or prior to being embedded in paraffin.

In the first of these procedures, the distance in time and space is short and the container shown in FIG. 1 is transferred to the pathological laboratory with reference to FIG. 2, at such laboratory the laboratory assistant releases the sample from the liquid manually, with the aid of a spatula 5 or like instrument, and then transfers the sample, supported on the spatula and a surrounding minor volume of liquid, to a shell mould 6 characteristic of the invention. The mould is compression moulded or injection moulded from a plastic material and has a recess 7 with a bottom 8 which serves as a support surface for a freeze table 9 of known kind. The freeze table 9 has planar end surfaces, of which one end surface, on which the tissue sample is frozen, is smooth.

Figure 3:
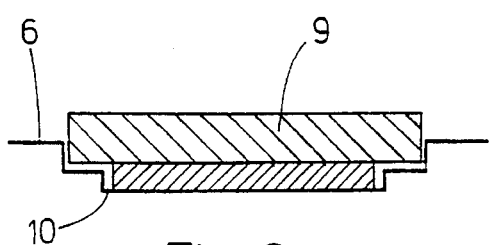
FIG. 3 is a cross-sectional view taken on the line III—III in FIG. 2.
Figure 4:
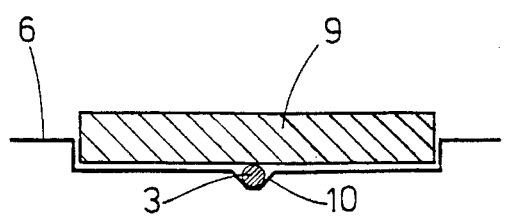
FIG. 4 is a cross-sectional view taken on the line IV—IV in FIG. 2.

Provided in the bottom 8 of the recess 7 is a cavity 10 whose cross-section corresponds substantially to the cross-section of the tissue sample. In the illustrated embodiment, the cavity 10 has a v-shaped cross-section with a flat bottom part. The top of the recess 7 terminates in a flange 11. The configuration of the recess 7 is normally different to the configuration of the freeze table, although the recess and the table can be adapted to one another, as illustrated in the drawings. The tissue sample 3 is transferred by means of the spatula 5 to the cavity 10, in which the sample is positioned so as to be level therein, i.e. so as to be oriented horizontally in a straight line. The upper part of the sample lies flush with the bottom 8 of the mould. A small volume of gel mentioned in the introduction and used when freezing-in the sample is applied to the bottom 8 of the mould. The freeze table 9 is then placed in the recess 7, such that the smooth end surface of the table will be in contact with the upper surface of the tissue sample, over the full length thereof. The mould together with sample and freeze table are then frozen instantaneously in a known manner, by submerging the mould into liquid nitrogen, for instance. FIGS. 3 and 4 illustrate mould, sample and freeze table in an assembled state.

Figure 5:
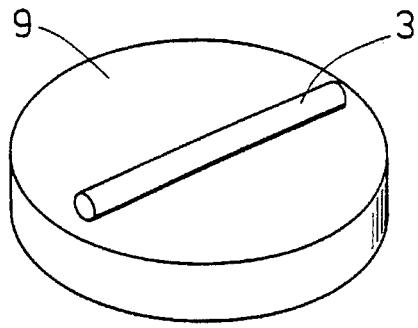
FIG. 5 is a perspective view of a freeze table having a sample tissue frozen thereon and ready to be cut into frozen sections in a microtome (not shown)
Figure 6:
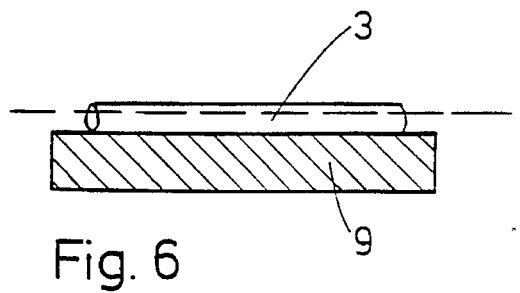
FIG. 6 is a side view of a frozen section taken from the sample tissue in FIG. 5.

Upon completion of this instaneous freezing process, the mould 6 is removed from the liquid nitrogen with the sample 3 frozen fast on the table 9 in the aforesaid levelled position, ready to be cut or sectioned as depicted in FIGS. 5 and 6. As will be seen, the entire length of the sample forms a continuous frozen section or slice. Several such continuous sections can thus be cut from one and the same tissue sample 3.

Figure 7:
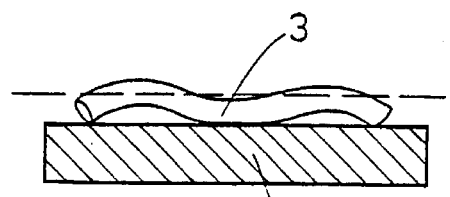
FIG. 7 is a side view of a tissue sample which has been frozen firmly to the freeze table with the aid of a conventional technique in a position of orientation in which it can be cut with the aid of a microtome.

FIG. 7 illustrates a tissue sample 3 which has been placed on the freeze table 9 with the aid of a conventional technique. The sample 3 has not been levelled, i.e. the sample is not oriented in a straight line in the horizontal plane. When a frozen section is cut, marked with the broken line in FIG. 7, two fragments of sample are obtained. This is unsatisfactory from the aspect of analysis.

In the second of the aforesaid two procedures, the distance in time and space between the place at which the sample is taken and the pathological laboratory is extensive or when the freeze process described above is not considered necessary. In order to protect the sample from damage during transportation, subsequent to depositing the sample in the manner described with reference to FIG. 1, the tube or container 1 is filled with a predetermined volume of fixative solution. According to one preferred embodiment, illustrated in FIG. 8, the volume of fixative solution used is equal to half the volume of the liquid 2. Under these conditions, the concentration of the fixative solution is also three times as high as the concentration normally used. In this way, the concentration of the fixative solution mixed with the liquid becomes the normal. The mixture of fixative solution and liquid will essentially fill the container 1 after the stopper 4 has been fitted. The tissue sample is transported in this state to the laboratory. A fixed sample 3 is distinguishable from a non-fixed sample in the laboratory solely by the volume of liquid present in the container. In unfavorable circumstances, this criterion may be insufficient to distinguish a fixed sample from a non-fixed sample. Consequently, a dye is introduced into the fixative solution in conjunction with fixing the sample. The dye and the fixative solution must not lave a toxic effect on the tissue sample and must not have an unfavorable influence on subsequent colouring of the sample in conjunction with its analysis. Furthermore, fixative solution mixed with the liquid should be isosmotic for the same reasons as those given above. The fixed sample is treated in a routine fashion subsequent to arriving at the laboratory.

The fixative solution used is formalin, glutaraldehyde, an alcohol-based solvent, or other conventional water-soluble fixative agents.

Figure 8:
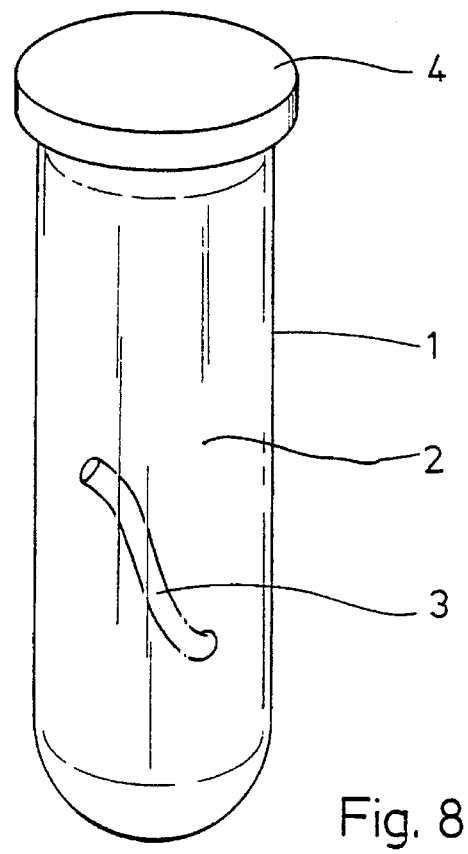
FIG. 8 is a perspective view of a container filled with fixative solution.

A sample that has been deposited in the manner illustrated in FIG. 1 or in FIG. 8 can also be deepfreezed and stored in a bank together with different tissue samples. Such a bank of tissue samples can be used for teaching and research purposes.

FIG. 9 to 13 illustrates another embodiment of the present invention in which like parts are designated by like reference numerals. In particular, FIG. 9 illustrates another embodiment of a shell mould 12 which is used when the tissue sample is embedded in paraffin subsequent to fixing and leaching the sample. Similar to the mould described above, the mould 12 of this embodiment includes a recess 13 having a bottom 14 in which a cavity 15 is provided. The cavity 15 has the same function as the cavity 7 in the mould 6 of FIG. 2. The mould also includes two upstanding side walls 16, 17 which function as guide elements for a carrier element 18 shown in FIG. 10. The carrier element includes circumferentially extending side walls 19, 20, 21 and 22 and a bottom wall 23 which is perforated with a number of openings 24.

The sample is placed in the cavity 15 and the carrier element 18 is then placed over the recess 13 and paraffin is poured from above into the carrier element 18 and runs down through the openings 24 and into the recess 13 and cavity 15. When the paraffin has solidified, the mould 12 is removed and the carrier element 18 turned upside down, such as to obtain the unit shown in FIG. 10. In considering the carrier element 18 or FIG. 11, the reference numeral 25 identifies a paraffin plateau, 26 identifies an elongated paraffin rod, and 27 identifies the tissue sample which is now oriented parallel with the horizontal plane on the top of the rod 26 of V-cross-section. When slicing the sample, it is only necessary to cut-away the relatively narrow paraffin rod 26 together with the sample.

FIG. 12 is a cross-sectional view of the mould 12 of FIG. 9. The mould may be made of stainless steel or a plastic material, or some other suitable material. The cavity 15 has a V-shaped cross-section with a flat bottom part.

FIG. 13 illustrates the assembly depicted 10 in cross-section in FIG. 11. The reference numeral 28 identifies the paraffin that remains on the upper side of the bottom wall 23 upon completion of the casting or embedding process. As depicted in FIG. 13 a continuous paraffin block is formed. It will also be seen from FIG. 13 that the bottom wall 23 and the openings 24 provided therein function to reinforce the paraffin block, and that the side walls serve to support the assembly as a whole when the assembly is placed on a table in the position shown in FIG. 11.

Although the invention has been described in the aforegoing with reference to tissue samples taken with the aid of needle biopsy assemblies, it will be understood that the samples can also be taken with other needle biopsy techniques, forceps or some other type of sampling instruments. One essential feature of the embodiment described above, however, is that the cavity provided in the mould has a configuration which coincides generally with the configuration of the tissue sample and that the sample is, in all cases, protected mechanically against dehydration. It will also be understood that the mould and its recess of the present invention may have a shape different to the illustrated cylindrical shape of mould 6 and recess 7 of FIG. 2. For example, these elements may have a generally rectangular shape similar to the corresponding mould 12 and recess 13 of the FIG. 9 embodiment, or may lave any other appropriate shape.

Similarly, the concentration and volume of the fixative liquid may be different to those recited. The container cap or stopper 4 may be provided with a screw thread for coaction with a corresponding internal screw thread provided on the upper part of the container 1.

In addition to the foregoing, unexpected results have been noted regarding the cell toxic characteristics and certain other cell effects of the liquid described herein on HeLa cells; that is, on a human transformed cell-line. In particular, analysis of HPMC in an aqueous phosphate buffered solution as described herein was carried out by the MIT-24 method which is well known in the art. The MIT-24 method has been used for years in studies of pharmaceuticals, plasticizers, foodstuffs, chlorine phenol and many other chemical compounds and will therefore not be described herein in detail except to note that it is a cell toxic test where effects of various substances on HeLa cells may be microscopically examined after 24 hours incubation, and also microscopically and metabolically examined after 7 days incubation. The metabolically topical determination may be typically made by the pH-indicator phenol red.

Two trials were made, each trial being performed with three parallel dilution series using HeLa cells grown in Parker's 199 medium with 5% fetal and streptomycin/penicillin in accordance with the MIT-24 method. It was noted that the toxicity on the HPMC solution was extraordinarily low. In particular, the 50% inhibitory concentration was over or equal with 50 volume percent. This unexpected result was noted for the 24 hour reading in connection with the inhibition of cell spreading, and also for the 7 day reading in connection with the inhibition of anaerobic metabolism.

In addition, the HPMC solution exhibited an extraordinary positive effect on cell cultures. In the interval of 17 vol. % to 0.62 vol. %, the HPMC solution had a growth increasing effect in which the cultures grew out faster than the controls after 24 hours (1/1 instead of 1/4 monolayer) with refined morphological architecture and remarkable little debris. In the same concentration interval, after 7 days a "preservative" effect was clearly noticeable. Unexpectedly, degeneration of the control cultures in the HPMC-affected cultures did not occur, the cell carpet in the HPMC cultures looked as fresh after 7 days as after 24 hours, and the metabolism was increased after 7 days. It is believed that all of the foregoing characteristics provide a substantial positive affect on cell life.

In view of the foregoing unexpected results, in addition to preserving tissue samples taken with the aid of a sampling instrument, the present invention is useful in handling cells, embryos, oocytes, bacterial samples, viral samples, serum, organ samples and other applications which relate to the handling of biologic matter where the preservation of morphologic characteristics is important. For example, the container 1 and liquid 2 of FIG. 1 are also of use in the handling of a specimen 3 such as biologic matter in the form of a bacterial sample. In particular, the biologic matter is collected in the usual manner and then transferred to the gel 2 of the present invention in the container 1 such that the biologic matter is suspended in such gel. In the handling of such biologic matter in gel 2 damage to the biologic matter caused by shocks and mechanical trauma is substantially eliminated and the morphologic characteristics of the biologic matter are preserved. It will be apparent to those skilled in the art that the shape and size of the container 1 will depend upon the nature of the particular biologic matter to be suspended in the gel 2; that is, whether the biologic matter is in the form of cells, embryos, oocytes, bacterial samples, viral samples, serum, organ samples, and the like.

The embodiments which have been described herein are but some of several which utilize this invention and are set forth here by way of illustration but not of limitation. It is apparent that many other embodiments which will be readily apparent to those skilled in the art may be made without departing materially from the spirit and scope of this invention.

We claim:

1. In a device for handling a tissue sample which has been taken for analysis with the aid of a biopsy needle, comprising a container and a liquid in the container, wherein the improvement comprises said liquid consisting essentially of an aqueous viscoelastic solution of cellulose ether, and optionally containing at least one of a buffer, sodium chloride, potassium chloride, a fixative and a dye, isosmotic with said tissue sample, atoxic, mixable with one of water and alcohol-based solvents, pyrogen free, sterile and freezable without the formation of crystals, the density and the pH of said liquid being about equal to the density and pH, respectively, of said tissue sample.

2. The device of claim 1, wherein said cellulose ether is a material selected from the group consisting of hydroxypropyl methyl cellulose, carboxymethyl cellulose, and ethyl hydroxyethyl cellulose.

3. The device of claim 1, wherein said cellulose ether is hydroxypropyl methyl cellulose.

4. The device of claim 3, wherein said hydroxypropyl methyl cellulose is present in about 1.8% by weight in said liquid.

5. The device of claim 1 wherein said solution contains a buffer.

6. The device of claim 5 wherein said buffer is a phosphate buffer.

7. The device of claim 4 wherein said liquid contains about 98.2% phosphate buffered solution of distilled water buffered with about 0.654 gram/liter $KH_2PO_4$, about 0.654 gram/liter KC1 and about 9.00 grams/liter NAC1.

8. The device of claim 7 wherein the pH of said liquid is about 7.4.

9. The device of claim 1 wherein said liquid contains said fixative.

* * * * *